(12) United States Patent
Jeong et al.

(10) Patent No.: US 7,807,201 B2
(45) Date of Patent: Oct. 5, 2010

(54) ANTIFUNGAL AGENT COMPRISING NATURAL PLANT EXTRACTS

(75) Inventors: Chang Hwa Jeong, Pusan (KR); Kyoung Dong Jeon, Pusan (KR); Moon Hyu Yang, Jeju (KR); Won Suk Kim, Pusan (KR); Kyung Chool An, Pusan (KR); Back Chun Lee, Pusan (KR)

(73) Assignee: Binex Co., Ltd., Pusan (KR)

( * ) Notice: Subject to any disclaimer, the term of this patent is extended or adjusted under 35 U.S.C. 154(b) by 5 days.

(21) Appl. No.: 11/751,476

(22) Filed: May 21, 2007

(65) Prior Publication Data

US 2007/0269535 A1 Nov. 22, 2007

(51) Int. Cl.
*A61K 36/00* (2006.01)

(52) U.S. Cl. ..................................... 424/725
(58) Field of Classification Search ............... None
See application file for complete search history.

(56) References Cited

U.S. PATENT DOCUMENTS 3,551,566 A * 12/1970 Masanao et al. ............ 514/336

OTHER PUBLICATIONS

Brocklebank et al.: Mycotic Enterocolitis of Atlanic Salmon Parr in a Hatchery in British Columbia.: Can Vet J.: vol. 40, Dec. 1999.: pp. 888-889.*

Phongpaichit et al. : Antimicrobial Activities of the Crude Methanol Extract of Acorus Calamus Linn: 2004. pp. 518-523.*
Florahealth.com Nov. 17, 2002. Retrieved from the internet: <http://web.archive.org/web/20021117095226/http://www.florahealth.com/Flora/home/canada/HealthInformation/encyclopedias/Calamus.asp>. Retrieved on Mar. 6, 2008.*
Hussein et al. Antimycotic Activity of Eugenol Against Selected Water Mold. Journal of Aquatic Animal Health. 2000. 12. Abstract.*
Philipson. New Drugs From Nature-It Could Be Yew. Phytotherapy Research.13,1999. pp. 2-8.*
Revilla et al. Comparison of Several Procedures Used for the Extraction of Anthocyanidins From Red Grapes. j. Agric. Food Chem. 1998. 46. pp. 4592-4597.*
Myint et al. Gas Chromatographic Determination of Eugenol in Ethanol Extract of Cloves. Journal of Chromatography. B. 679. 1996. 193-195.*
Hussein et al. Antimycotic Activity of Eugenol Against Selected Water Mold. Journal of Aquatic Animal Health. 2000. pp. 224-229.*

* cited by examiner

*Primary Examiner*—Patricia Leith
*Assistant Examiner*—Melenie McCormick
(74) *Attorney, Agent, or Firm*—The Nath Law Group; Joshua B. Goldberg; Mihsuhn Koh

(57) ABSTRACT

An antifungal agent for the prevention and treatment of the fungal diseases caused by the water mould *Saprolegnia parasitica* includes the natural product sweet flag extract or its essential oil as an active ingredient and, therefore, is eco-friendly and not harmful to fish. In addition to offering effective prevention and inhibition of mould growth, the antifungal agent can replace malachite green, a known carcinogen, in the aquaculture industry.

1 Claim, 4 Drawing Sheets

ANTIFUNGAL AGENT COMPRISING NATURAL PLANT EXTRACTS

CROSS-REFERENCE TO RELATED APPLICATIONS

The benefit of priority is claimed to Republic of Korea patent application 2006-0045588, filed May 22, 2006, the entire contents of which are incorporated herein by reference.

BACKGROUND

1. Field of the Invention

The present invention relates to an antifungal agent for the prevention and treatment of aquatic fungal infections comprising the essential oil of sweet flag, which is a natural plant extract developed to replace existing chemical agents such as malachite green or antibiotics used for the prevention and treatment of aquatic fungal infections in aquaculture. More particularly, the present invention relates to an antifungal agent having a superior effect for the prevention and treatment of aquatic fungal infections when compared with malachite green, which is known as carcinogen and banned from use.

2. Description of the Related Art

In general, the fertilization of eggs in aquaculture refers to the mass production of fertilized eggs under human control in a restricted area. It is a stage prior to the production of larval fish. Aquatic fungal infections have been known since long ago. Although healthy fish are seldom infected, water moulds proliferate on the dead cells at the inflammation or wound of unhealthy fish like fluffs. Such aquatic fungal infection is caused by the proliferation of the phycomycete *Saprolegnia parasitica* at the wound. The infection prevails in spring when the water temperature becomes 14° C. or higher. It persists through the year excluding the high water temperature period. It disappears when the water temperature increases over 20° C. The infection is caused by the parasitization of water moulds at the wounds formed during the transfer of fish, selection, egg collection, sperm harvesting, etc., parasitizations by skin flukes (*Gyrodactylus*), lernea, etc., inflammations caused by such pathogenic bacteria as *Aeromonas hydrophila*, inflammations caused by nutritional diseases or abnormal body surfaces caused by bad health. Typically, it invades the epithelial tissue and proliferates hypha, causing the fish to die. Also, it causes the loss of appetite and lets the fish break away from the group. The water moulds proliferating in dead fish eggs surround the living eggs and suffocate them.

Until recently, various antibiotics and chemical agents like malachite green have been used improperly in order to remove the water moulds that parasitize fish or fertilized eggs and cause them to perish. Among them, malachite green ($C_{23}H_{25}ClN_2$) is a light bluish-green, triphenylmethane-based basic dye usually used for the staining of fiber, wood, paper, straw and other materials. It has also been used as reagent or indicator in analytical chemistry. Also, it has been used as topical antiseptic in the field of medicine. Particularly, it has been used to prevent infections by fungi or bacteria during sterilization of fertilized eggs, culturing, transfer and storing in aquaculture since it is effective against fungi and Gram-positive bacteria. However, suspected as a carcinogen, its use is banned in many countries.

Antimould agents and antifungal agents are used to treat fungi. These agents are classified into the following two groups: (1) those that chemically affect the cell wall or cell membrane of fungi and interrupt the normal enzymatic functions of the cells; and (2) those that penetrate the cell wall or cell membrane and inhibit the enzymatic actions including nucleic acid and protein synthesis. Industrially, the group (1) antimould agents that disturb the cell wall or cell membrane are used in general. Antifungal agents are agents for controlling pathogenic fungi. Use of the agents has increased with the abrupt increase of fungal infections. A lot of pesticides are being developed in the phytopathological field to destroy pathogenic moulds harmful to the crops. At present, copper compounds and dithiocarbamate compounds are used worldwide. In addition, formaldehyde, copper sulfate, methylene blue, bithionol, oxolinic acid, potassium permanganate, calcium hypochlorite, calcium hydroxide, antibiotics (chloramphenicol, oxytetracycline, chlortetracycline), sulfa drugs (sulfamerazine, sulfamonomethoxine, sulfadimethoxine sodium), and so forth are currently used in the aquaculture industry to reduce the damage caused by fungi. But, as suggested by many researches, these substances may be very harmful to both human body and environment. Accordingly, researches are being carried out on various physiologically active materials and antifungal substances existing in the nature.

SUMMARY

The present inventors have worked to find out a natural substance that can replace the aforesaid chemicals. In doing so, they completed the present invention by discovering the antifungal effect of sweet flag against water moulds. The antifungal agent comprising sweet flag extract is expected to replace the conventional antibiotic malachite green.

Accordingly, an object of the present invention is to provide an antifungal agent comprising safe natural products only which is capable of improving industrial value and removing the side effects of chemical agents used to prevent fungal infections in fish through the superior effect of inhibiting and removing water moulds.

DETAILED DESCRIPTION

Figure 1:
FIG. 1 shows the antifungal effect of sweet flag extract tested by the 24-well plate method.

To attain the aforesaid object, the antifungal effect of sweet flag extract against water moulds was verified and an economically available viable product was developed.

In accordance with an embodiment of the present invention, provided is an antifungal composition for the treatment of fungal infections in fish which comprises sweet flag extract as active ingredient.

Sweet flag (*Acorus calamus*) is a perennial plant from the Araceae family. It has scented rhizomes, leaves and roots. Commonly, its roots have been used medicinally. Its rhizome contains essential oil, tannin, starch, palmitiic acid, vitamin C, and so forth. The essential oil contains asarone, eugenol, eugenol, sesquiterpene, and so forth. Sweet flag has long been used in folk remedies. It facilitates the secretion of gastric juice and hydrochloric acid in the stomach, helps digestion and is effective in treating diarrhea, ear inflammations, skin diseases, athlete's foot, pains, spasm, cough, phlegm, body temperature drop and blood circulation problems. In the West, it has been used as vermicide, tonic and perfume (*Bo Sup Chung, Min-Gyo Shin*, Folk Medicine Encyclopedia, Younglim Publishing, pp. 278-280, 1998).

The sweet flag extract may be extracted using water, a hydrophilic organic solvent or a mixture solvent thereof. Preferably, it is extracted using a hydrophilic organic solvent. The hydrophilic organic solvent may be diluted with 50% to 100% of water.

Examples of the hydrophilic organic solvent that can be used in the present invention include $C_1$-$C_5$ low alcohol such as methanol, ethanol, propyl alcohol, isopropyl alcohol, etc.; $C_2$-$C_5$ low aliphatic ketone such as acetone, methyl ethyl ketone, etc.; and $C_2$-$C_5$ low polyhydric alcohol such as 1,3-butylene glycol, propylene glycol, glycerine, etc. With hydrophilic alcohol groups (OH) or ketone groups (COC), they have similar polarity and provide similar extraction activity for the solute.

In addition to the sweet flag extract, the composition for the treatment of fungal infections in fish according to the present invention may further comprise a pharmaceutically acceptable diluent or excipient.

In the present invention, preferably, an antifungal composition for the treatment of fungal infections in fish which has antifungal activity against the water mould *Saprolegnia parasitica*, which causes fungal diseases in fish, is provided. The antifungal activity against the water mould was tested ad described below.

The antifungal composition of the present invention may be administered to a fish using techniques well known to those of ordinary skill in the art, for example by adding the antifungal composition into a water pool comprising a fish. In the specification, the "effective amount" designates an amount sufficient to treat fungal infections in fish. Determination of the effective amounts is within the capability of those skilled in the art, especially in light of the detailed disclosure provided herein.

The major ingredients of the natural product sweet flag are summarized in Table 1.

TABLE 1

Major ingredients of sweet flag extract

| | Major ingredients |
|---|---|
| Sweet flag | tannin, vitamin C, acorin, palmitic acid, starch, eugenol, asarylaldehyde, asarone, shyobunone, epishyobunone, isoshyobunone, calamendiol, isocalamendiol, calacone, acorone, acoronene, acorenone, α-pinene, camphene, camphor, borneol, calamene, caryophyllene, elemene, curcumin, selinene, acolamone, isoacolamone |

The key functions of these ingredients are given in Table 2. As shown in Table 2, the ingredients of the natural product have antifungal activity and the effect of inhibiting and removing water moulds.

TABLE 2

Key functions of sweet flag extract

| Major ingredients | Key functions |
|---|---|
| Asarone ($C_{12}H_{16}O_3$) | Strong antiviral and antifungal activity, antiseptic activity, blood circulation promotion, blood pressure increase, tonification |
| Eugenol ($C_{10}H_{12}O_2$) | Antioxidation activity, antifungal activity, sterilization, antimould activity, choleretic activity, antiviral activity, antiseptic activity |

The sweet flag extract further contains shyobunone, calamene, acorone and camphene. In general, the antifungal and antibacterial effect of the essential oil is determined by the activity and content of its ingredients—terpene oxide, ester, alcohol, phenol, aldehyde, ketone, monoterpene, sesquiterpene, etc. These ingredients of the essential oil have very complicated molecular structure and are known to have antiviral, antifungal and antimould activity. Further, they are known to facilitate efficient blood circulation and stabilizes the nerve, in addition to providing choleretic and tonifying activity.

EXAMPLES

The present invention is further illustrated by the following examples. However, the following examples are presented for the understanding of the present invention and the present invention is not limited to the details thereof.

Example 1
Preparation of Sweet Flag Extract

Rhizomes of sweet flag dried in sunlight were extracted in at least one solvent selected from the group consisting of water, ethanol, isopropyl alcohol, methanol, propanol, butanol, glycerine and butylene glycol, preferably in ethanol. The antifungal agent in accordance with the present invention comprises 1-50 wt % of the sweet flag extract.

Example 2
Identification and Subculture of Pathogenic Water Moulds (*Saprolegnia parasitica*.)

Water moulds were taken from the body surface of rainbow trout. The water moulds were isolated and subcultured using GY medium (broth) containing 10 g/L of glucose and 2.5 g/L of yeast extract and GY medium (agar) containing 10 g/L of glucose, 2.5 g/L of yeast extract and 7.5 g/L of agar. The pathogenic water moulds were isolated and identified as *Saprolegnia parasitica* (Gene Bank Data homology search result: 99%) through ITS-5.8S rDNA sequencing at the Korean Culture Center of Microorganisms (KCCM) of the Korean Federation of Culture Collections (KFCC). The natural product sweet flag extract was compared with malachite green. Antifungal effect and minimal inhibitory concentration (MIC) were tested by the 24-well plate method and the diffusion method.

Figure 2:
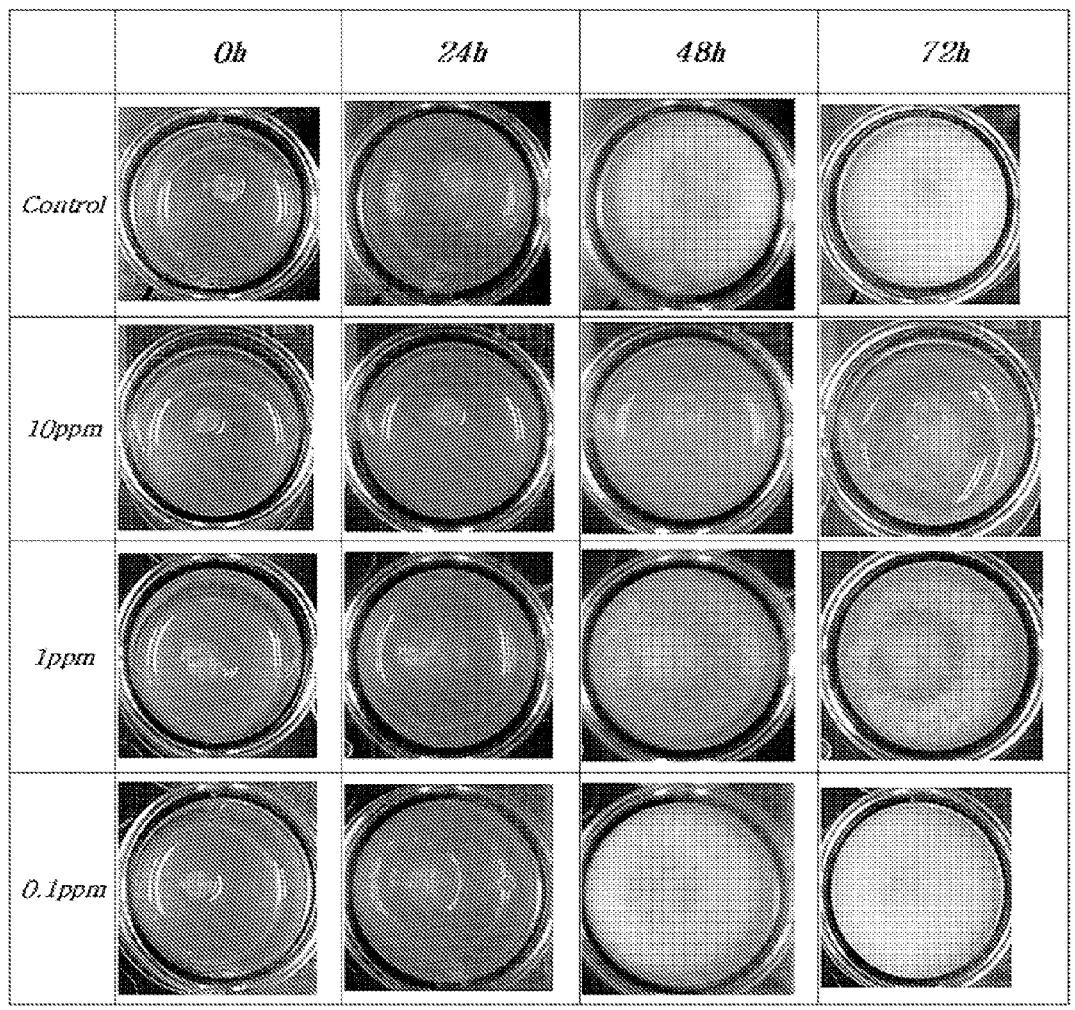
FIG. 2 shows the photographs taken every 24 hours to verify the antifungal effect of sweet flag extract.

Test Example 1
Test of Antifungal Effect at Different Concentrations of Sweet Flag Extract by 24-Well Plate Method GY agar was placed on a sterilized 24-well plate. After waiting until the medium was dry, each 100 μL of 10 ppm, 1 ppm and 0.1 ppm sweet flag extract was added to the GY medium (control), as seen in FIG. 1. Hyphae of *Saprolegnia parasitica*, which had been cultured in GY agar plate, taken with a 50 mL syringe were added to each plate and antifungal activity test was carried out for 72 hours. Photographs were taken every 24 hours. FIG. 1 shows the antifungal activity when the 24-well plates were kept in a 20° C. incubator. FIG. 2 shows the growth inhibition and removal effect against the water moulds when the sweet flag extract was added.

Figure 3:
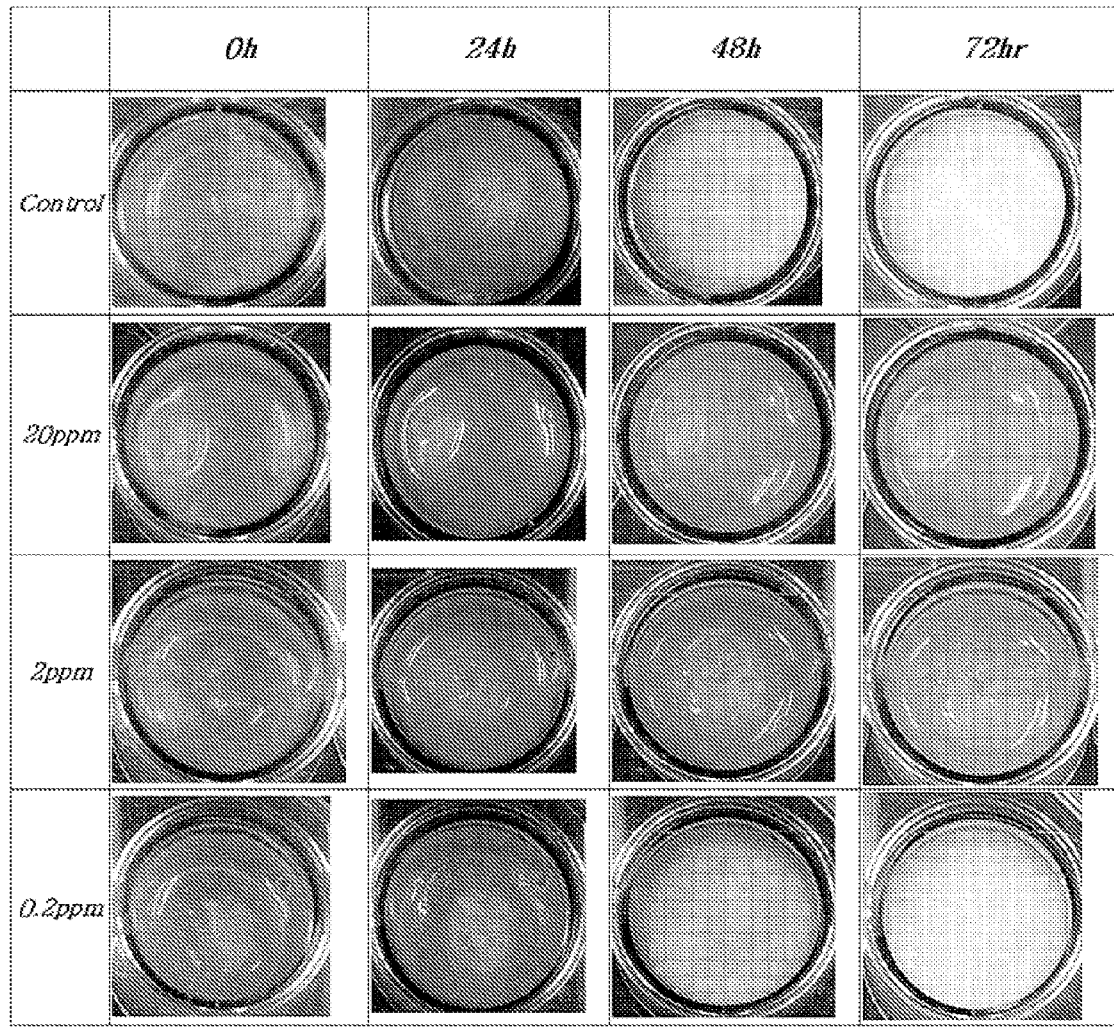
FIG. 3 shows the antifungal effect of malachite green tested by the 24-well plate method.

Test Example 2
Test of Antifungal Effect at Different Concentrations of Malachite Green (MG) by 24-Well Plate Method GY agar was placed on a sterilized 24-well plate. After waiting until the medium was dry, each 100 μL of 20 ppm, 2 ppm and 0.2 ppm malachite green (MG) was added to the GY medium (control), in the same manner as in FIG. 1. Hyphae of *Saprolegnia parasitica*, which had been cultured in GY agar plate, taken with a 50 mL syringe were added to each plate and antifungal activity test was carried out for 72 hours. Photographs were taken every 24 hours. FIG. 3 shows the growth inhibition and removal effect against the water moulds when the malachite green (MG) was added.

Test Example 3
Test of Antifungal Effect by Diffusion Plate Method

Figure 4:
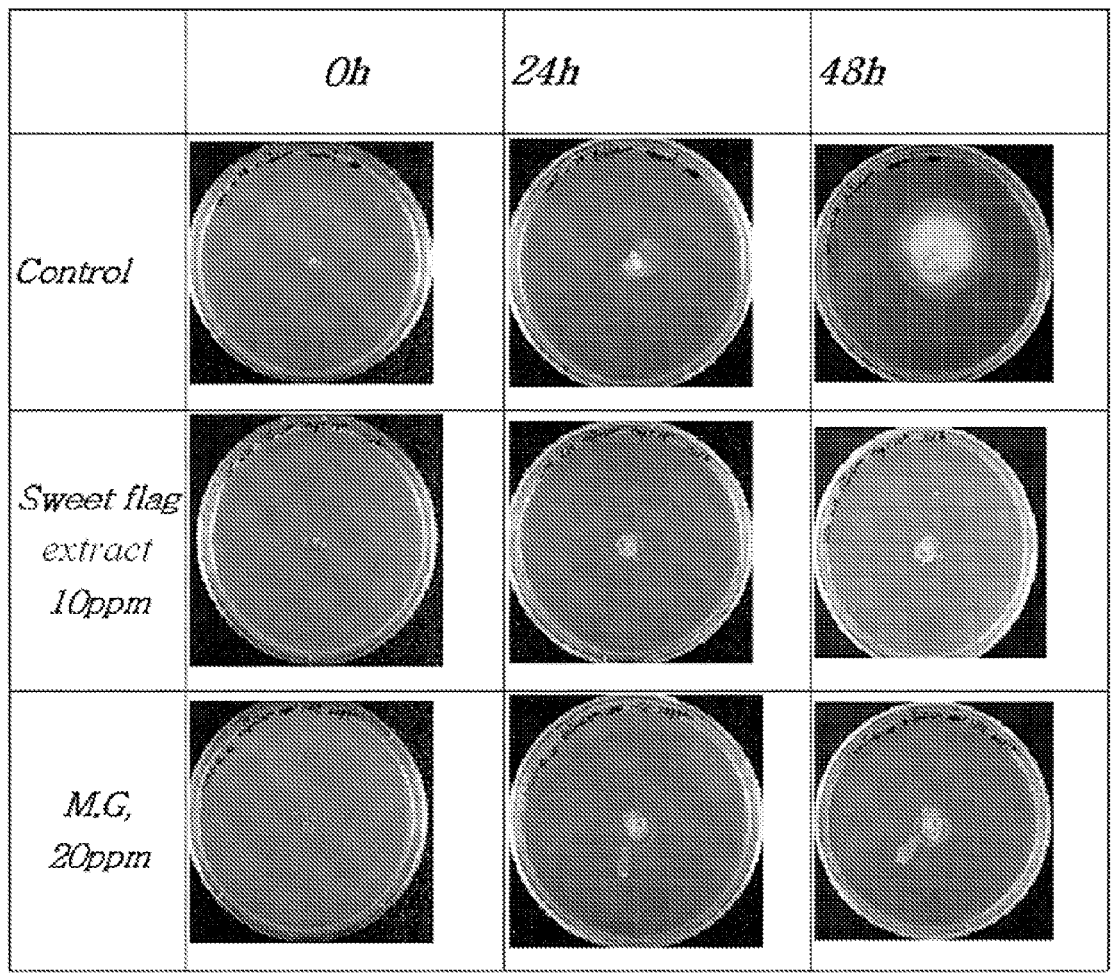
FIG. 4 shows the antifungal effect of sweet flag extract and malachite green (MG) tested by the diffusion plate method.

The center of the GY agar plate was cut to a diameter of 5 mm and the agar was removed. Each 20 μL of 10 ppm sweet flag extract, 20 ppm malachite green and GY medium (control) was added to the cut area. Hyphae of *Saprolegnia parasitica*, which had been cultured in plate medium, taken with a 50 mL syringe were added to each plate and antifungal activity test was carried out for 48 hours. Photographs were taken every 24 hours. FIG. 4 shows the growth inhibition and removal effect against the water moulds when the sweet flag extract and the malachite green were added. Table 3 shows the antifungal effect of sweet flag extract and malachite green (MG) based on MIC. For each concentration, the antifungal effect was evaluated as high, moderate and low.

TABLE 3

Antifungal effect of sweet flag extract and malachite green (MG)

| Kinds | Antifungal effect (high: +++ medium: ++ low: +, not-measured: *) | | | | | | | | | | | | |
|---|---|---|---|---|---|---|---|---|---|---|---|---|---|
| Conc. Of Sweet flag extract | 0.1 ppm | 1 ppm | 10 ppm | 20 ppm | 30 ppm | 40 ppm | 50 ppm | 60 ppm | 70 ppm | 80 ppm | 90 ppm | 100 ppm | 200 ppm |
| Effect | + | ++ | +++ | +++ | +++ | +++ | +++ | +++ | +++ | +++ | +++ | +++ | +++ |
| Conc. Of MG | 0.2 ppm | 2 ppm | 20 ppm | * | * | * | * | * | * | * | * | * | * |
| Effect | + | ++ | +++ | | | | | | | | | | |

Concluding the well plate method and diffusion plate method results given in FIG. 2, FIG. 3, FIG. 4 and Table 3, the antifungal effect against the water mould (*Saprolegnia parasitica*) was highest for 10 ppm sweet flag extract. It was comparable to the effect obtained with 20 ppm MG. The MIC of sweet flag extract and MG are expected to be 10 ppm and 2 ppm, respectively.

CONCLUSION

As described, the natural product sweet flag extract has superior effect for the treatment of fungal infections in fish. Thus, the natural product extract is expected to replace the chemical agents used to treat fungal diseases in the aquaculture industry and to offer good economical advantages. Further, at this point of time when fish are emerging as the future's food resources, the eco-friendly fish disease treatment provided by the present invention can solve the problem of the accumulation of harmful chemical agents in fish.

Those skilled in the art will appreciate that the concepts and specific embodiments disclosed in the foregoing description may be readily utilized as a basis for modifying or designing other embodiments for carrying out the same purpose of the present invention. Those skilled in the art will also appreciate that such equivalent embodiments do not depart from the spirit and scope of the present invention as set forth in the appended claims.

What is claimed is:

1. A method for treatment of *Saprolegnia parasitica* infections in fish comprising: administering to fish in need thereof, an effective amount of an antifungal composition comprising sweet flag extract as an active ingredient, wherein said extract of sweet flag is selected from one or more of: a water extract of sweet flag, a $C_1$-$C_5$ lower alcohol extract of sweet flag, a $C_2$-$C_5$ lower aliphatic ketone extract of sweet flag and a $C_2$-$C_5$ lower poylhydric alcohol extract of sweet flag.

* * * * *